United States Patent [19]
Kunos et al.

[11] Patent Number: 5,939,429
[45] Date of Patent: Aug. 17, 1999

[54] CARDIOVASCULAR USES OF CANNABINOID COMPOUNDS

[75] Inventors: George Kunos, Bethesda, Md.; Karoly Varga; Jens Wagner, both of Richmond, Va.; Earl F. Ellis, Midlothian, Va.; Aron Sanyal, Mechanicsville, Va.

[73] Assignee: Virginia Commonwealth University, Richmond, Va.

[21] Appl. No.: 09/161,751

[22] Filed: Sep. 29, 1998

Related U.S. Application Data

[60] Provisional application No. 60/060,425, Sep. 30, 1997.
[51] Int. Cl.$^6$ .......... A61K 31/44; A61K 31/535; A61K 31/40; A61K 31/405; A61K 31/38
[52] U.S. Cl. .......... 514/298; 514/235.5; 514/414; 514/415; 514/443
[58] Field of Search .................. 514/298, 235.5, 514/414, 415, 443

[56] References Cited

U.S. PATENT DOCUMENTS

| | | | |
|---|---|---|---|
| 5,532,237 | 7/1996 | Gallant et al. | 514/235.2 |
| 5,605,906 | 2/1997 | Lau | 514/298 |
| 5,747,524 | 5/1998 | Cullinan et al. | 514/443 |

*Primary Examiner*—Raymond Henley, III
*Attorney, Agent, or Firm*—Whitham, Curtis & Whitham

[57] ABSTRACT

Hemorrhagic shock and in other conditions associated with excessive vasoconstriction, such as hypertension, peripheral vascular disease, cirrhosis of the liver, or certain forms of angina pectoris can be treated by using agonists of CB1 receptors as well as other cannabinoid receptors. In addition, it has been determined that in septic shock and cirrhosis of the liver when hypotension is due to activation of macrophages by bacterial endotoxin, the use of a drug that selectively blocks CB1 receptors or other cannabinoid receptors may be of therapeutic value by preventing or attenuating the endotoxin-induced hypotension.

7 Claims, 11 Drawing Sheets

CARDIOVASCULAR USES OF CANNABINOID COMPOUNDS

CROSS-REFERENCE TO RELATED APPLICATIONS

This application is a continuation-in-part (CIP) application of U.S. Provisional Patent Application Serial No. 60/060,425 filed Sep. 30, 1997, and the complete contents of that application is herein incorporated by reference.

DESCRIPTION

BACKGROUND OF THE INVENTION

1. Field of the Invention

The invention relates to the cardiovascular effects of cannabinoid compounds, i.e. naturally occurring as well as synthetic substances that bind with high affinity to cannabinoid receptors in the brain and in peripheral tissues of mammals, including man.

2. Description of the Prior Art

Naturally occurring cannabinoids may be divided into two categories, plant-derived and endogenous. Plant-derived cannabinoids are known to elicit dramatic psychobehavioral effects, exemplified by the well-known $\Delta^9$-tetrahydrocannabinol (THC), the psychotropic principle in marijuana. They are also known to have complex cardiovascular effects, a prominent component of which is hypotension (Vollmer et al. *J. Pharm. Pharmacol.* 1974, 26:186–198) Endogenous cannabinoids (endocannabinoids) are a class of lipid-like molecules that share receptor binding sites with plant-derived cannabinoids and mimic many of their neurobehavioral effects (Mechoulam et al. *Adv. Exp. Bio. Med.* 1996, 402:95–101.) Two endocannabinoids have been characterized in some detail: arachidonyl ethanolamide (anandamide) (Devane et al. *Science* 1992, 258:1946–1949; Felder et al. *Proc. Natl. Acad. Sci. USA.* 1993, 90:7656–7660) and 2-arachidonyl glyceride (2-AG) (Mechoulam et al. *Biochem. Pharmacol* 1995, 50:83–90). Like plant-derived cannabinoids, both anandamine and 2-AG are capable of eliciting hypotension (Varga et al. *FASEB J.* 1998, 12:1035–1044; Varga et al. *Eur. J. Pharmacol.* 1995, 278:279–283; Stein et al. *Br. J. Pharmacol.* 1996, 119:107–114; Varga et al. *Hypertension* 1996, 28:682–688; Lake et al. *Hypertension* 1997, 29:1204–1210; Calignano et al. *Eur. J. Pharmacol.* 1997, 337: R1–R2). In addition, various cannabinoid compounds have been produced synthetically.

Cannabanoids exert their effects by binding to specific receptors located in the cell membrane. To date, two types of high-affinity cannabinoid receptors have been identified by molecular cloning: 1) CB1 receptors, present mostly in brain (Devane et al. *Mol. Pharmacol.* 1988, 34:605–613; Matsuda et al. *Nature* 1990, 346:561–564) but also in some peripheral tissues (Shire et al. J. Biol. Chem. 1995, 270:3726–3731; Ishac et al. *Br. J. Pharmacol.* 1996, 118:2023–2028), and 2) CB2 receptors, present on macrophages in the spleen (Munro et al. *Nature* 1993, 365:61–65).

The physiologic roles of endogenous cannabinoids and the pathways by which those roles are implemented are the subject of intense investigation. The observation that cannabinoids induce hypotension suggests a potential role for these substances in cardiovascular function. The results of a recent study by Lake et al.(*J. Pharmacol. Exp. Ther.* 1997, 281:1030–1037) lends credence to this idea. The study suggested that, when injected into anesthetized or conscious rats, anandamide and other cannabinoid substances cause profound hypotension mediated by peripheral CB1 receptors present in the heart and vasculature. However, further direct links between the endogenous cannabinoids and cardiovascular functions have been wanting. Results which are described herein supply that link and form the basis for the invention of a method described below whereby cannabinoid compounds can be used to ameliorate pathological conditions associated with hemodynamic abnormalities.

SUMMARY OF THE INVENTION

This invention provides a method for the treatment of pathological states related to hemodynamic abnormalities such as hypotension and hypertension using cannabinoids or cannabinoid-related compounds. The impetus for the invention depended directly on the development of a novel concept of the role of endogenous cannabinoids and their receptors in the control of cardiovascular functions, such as blood pressure, and thus the implication of their involvement in various pathological states associated with hypotension and hypertension.

We have recently reported two related lines of investigation, both of which demonstrate that endocannabinoids and their receptors may be directly involved in the control of cardiovascular functions, such as blood pressure. The first study (Wagner et al. *Nature* 1997, 390:518–521) showed that, in anesthesized rats, hypotension caused by hemorrhagic shock was accompanied by the production of the endogenous cannabanoid anandamide by circulating macrophages. When macrophages were isolated from animals in hemorrhagic shock and administered to normal control rats, hypotension was elicited in the recipient rats. In addition, the selective CB1 receptor antagonist SR141716A, when administered systemically to animals in hemorrhagic shock, caused a marked and prolonged increase in blood pressure. However, when SR141716A was administered centrally (i.e. directly into the brain, thus not reaching peripheral blood vessels) no such effect was observed. These results taken together suggest that the activation of peripheral (vascular) CB1 receptors contributes to hemorrhagic shock, and that anandamide produced by macrophages may be a mediator of this effect. The observed results were found to be independent of changes in nitrous oxide synthase (NOS) activity and circulating levels of nitrosothiols and thus may not be explained by mechanisms related to either of those substances. Significantly, pretreatment of the rats with anandamide-like cannabinoid agonists prolonged their survival, whereas pretreatment with SR141716A shortened survival. This suggests that the activation of CB1 receptors is beneficial for survival in hemorrhagic shock, probably because the attendant hypotension counters the excessive compensatory vasoconstriction that occurs following hemorrhage. Therefore, we propose that the use of CB1 receptor agonists may be of value in the treatment of hemorrhagic shock and in other conditions associated with excessive vasoconstriction, such as hypertension, peripheral vascular disease or certain forms of angina pectoris.

Our second study (Varga et al. *FASEB J.* 1998, 12:1035–1044) was directed toward elucidation of the mechanism of hypotension induced by endotoxic (septic) shock. Endotoxic shock is a potentially lethal failure of multiple organs that is initiated by lipopolysaccharide (LPS or 'endotoxin') present in the outer membrane of gram-negative bacteria. The primary cellular targets of LPS are macrophages, which are activated by LPS to generate various cytokines. Although some symptoms of septic shock have been attributed to the LPS-induced release of cytokines from circulating macrophages (Wright et al. *Science* 1990, 249:1431–1433; Dentener et al. *J. Immunol.* 150:2885–2891; Sherry and Cerami *J. Cell. Biol.* 1988, 107:1269–1277), pharmacological antagonism of cytokine effects fail to provide protection from the hypotension of septic shock (Stone *Science* 1994, 264:365–367; Nantason et al. *Ann. Int. Med.* 120:771–783). Some other mechanism must be responsible. Our study showed that hypotension and tachycardia develop in normal rats injected with bacterial endotoxin or with monocytes or blood platelets from another rat that had been treated with endotoxin. In both cases, the hypotension but not the tachycardia could be prevented by pretreatment of the recipient rats with the CB1 receptor antagonist SR141716A. Further experiments showed that when macrophages were isolated from normal rat blood and treated in vitro with LPS, the presence of anandamide could be documented by gas chromatography/mass spectrometry, whereas in LPS-treated platelets, the generation of 2-AG could be demonstrated. These findings indicate that macrophages and platelets generate different endogenous cannabanoids (anandamide and 2-AG, respectively) in response to stimulation by LPS and that both anandamide and 2-AG may be mediators of endotoxin-induced hypotension via activation of vascular CB1 receptors. Based on these findings, we propose that in septic shock and related pathological conditions, the use of a drug that selectively blocks CB1 receptors can be of therapeutic value by preventing or attenuating the endotoxin-induced hypotension.

Still more recent findings indicate that previously unknown SR141716A-sensitive receptors other than CB1 ('anandamine receptors') may be involved in endotoxic shock. We therefore propose that, in the treatment of septic shock and related pathological conditions, drugs which block this new class of receptor will also be of great utility.

BRIEF DESCRIPTION OF THE DRAWINGS

The foregoing and other objects, aspects and advantages will be better understood from the following detailed description of the preferred embodiments of the invention with reference to the drawings.

FIG. 1. The effects of monocytes/platelets isolated from 18 patients with septic shock and from healthy humans on the mean blood pressure (MP, top panel) and heart rate (HR, bottom panel) of anesthesized rats pretreated with vehicle (open circles) or with 3 mg/kg SR141716A (filled circles). Vertical bars indicate standard error. Note that the hypotensive effect of monocytes/platelets from septic patients was significantly inhibited by SR141716A (top, open vs. filled circles) whereas the tachycardic effect was slightly increased (bottom). Note also that cells from healthy humans had minimal effects on blood pressure and heart rate (open squares).

FIG. 2. The effects of monocytes/platelets from 9 patients with chronic cirrhosis on the mean blood pressure (MAP, top panel) and heart rate (HR, bottom panel) of rats pretreated with vehicle (open circles) or with 3 mg/kg SR141716A (filled circles). Note that the hypotensive effect of cells from cirrhotic patients was inhibited by SR141716A, whereas their tachycardic effect was not.

FIG. 3. Inhibition of the mesenteric vasodilator action of anandamide by SR141716A in the isolated, buffer-perfused rat mesenteric vascular bed (see Methods). Anandamide was administered as a bolus intra-arterial injection of the indicated dose in the absence (○) or presence of 0.5 $\mu$mol/L (▼) or 5 $\mu$mol/L (●) of SR141716A present in the perfusion medium. The antagonist was added to the medium 10 min. prior to the injection of anandamide. Points and vertical bars represent means±SE from 4 to 5 separate experiments.

FIG. 4. Dose-dependent mesenteric vasodilator or vasoconstrictor action of cannabinoid agonist and of arachidonic acid. Drugs were administered as close arterial bolus injections in a volume of 100 $\mu$l. Isolated mesenteric arterial bed preparations were perfused at a rate of 2 ml/min, with Krebs' buffer containing 12 $\mu$mol/L phenylephrine. Under these conditions, basal perfusion pressure was 80–100 mmHg. Points and vertical lines represent means±SE from 4–6 separate experiments. The drugs tested were anandamine (○), R-methanandamine (▽), HU-210 (◇), WIN 55,212-2 (□), 2-arachidonyl glycerol (Δ), $\Delta^9$-tetrahydrocannabinol (●), and arachidonic acid (■).

FIG. 5. The effect of endothelial denudation on the mesenteric vasodilator response to anandamide. The effect of 145 nmol of ananamide was tested in control (left) and endothelium denuded preparations (right), in the absence (open columns) or presence (striped columns) of 5 $\mu$mol/L SR141716A. * indicate significant differences (P<0.05) from corresponding values in the absence of antagonist. # indicates significant differences from corresponding values in control preparations. Columns and vertical bars represent means±SE from 5 to 7 experiments.

FIG. 6. The effect of 4 cannabanoid agonists on blood pressure of pentobarbital-anesthesized CB1 receptor knockout mice (−/− mice, open circles, n=4–6) and their genetically matched controls with intact CB1 receptors (+/+ mice, filled circles, n=4–6).

FIG. 7. The hypotensive effect of *E. coli* lipopolysacchaide (LPS) in CB1 receptor knockout −/− mice. Mice were anesthesized with sodium pentobarbital (50 mg/kg i.p.) and were then injected i.v. with 100 $\mu$g/kg LPS 10 minutes following the similar injection of vehicle (open circles) or 3 mg/kg SR141716A (filled circles). Note that LPS causes hypotension which is inhibited by SR141716A. Mean and standard errors are shown. The number of animals in each group is four.

FIG. 8. The structure of abnormal cannibidiol. For comparison, the structure of 4 other cannabinoids are also shown.

FIG. 9. The hypotensive effect of abnormal cannabinoid in anesthesized rats (top) and mice (bottom). Male Sprague-Dawley rats (300–350 g) were anesthesized with urethane (0.7 g/kg i.v.+0.3 g/kg i.p.), male ICR mice (25–28 g) were anesthesized with sodium pentobarbital, 50 mg/kg i.v. Polyethylene cannulae were inserted into the femoral vein (for drug injections) and artery (for monitoring of blood pressure). ΔMAP: change in mean arterial pressure. Points and vertical bars represent means±standard errors from 4–6 experiments. A: dose-dependent effect of abnCBD (i.v.) in rats. Significant hypotension is indicated by *. B: Effects of 10 mg/kg (i.v.) abnCBD in rats before (filled circles) and after treatment with 3 mg/kg SR141716A (open circles). Significant inhibition is indicated by #. C: The effect of 10 mg/kg (i.v.) abnCBD in ICR mice before (filled circles) and after treatment with 3 mg/kg SR141716A (open circles).

FIG. 10. The effect of abnormal cannabidiol on blood pressure in CB1 receptor knockout −/− mice. Mice were anesthesized with sodium pentobartital, 50 mg/kg i.p. and were pretreated with vehicle (open triangles) or 3 mg/kg i.v. SR141716A (filled triangles) before the i.v. injection of 20 mg/kg abnCBD. Note that abnCBD elicits hypotension which is inhibited by SR141716A. *indicates significant difference from corresponding control value.

FIG. 11. Abnormal cannabidiol causes dose-dependent mesenteric vasodilation, which is inhibited by pretreatment with SR141716A. Isolated, buffer-perfused rat mesenteric vascular beds were prepared as described by Varga et al. AbnCBD was injected intra-arterially as a bolus, in the absence or presence of 1 µM SR141716A in the buffer. Note that the marked vasodilator effect of 1 and 5 mg of abnCBD is completely blocked by SR141716A.

DETAILED DESCRIPTION OF THE PREFERRED EMBODIMENTS OF THE INVENTION

Figure 1A:
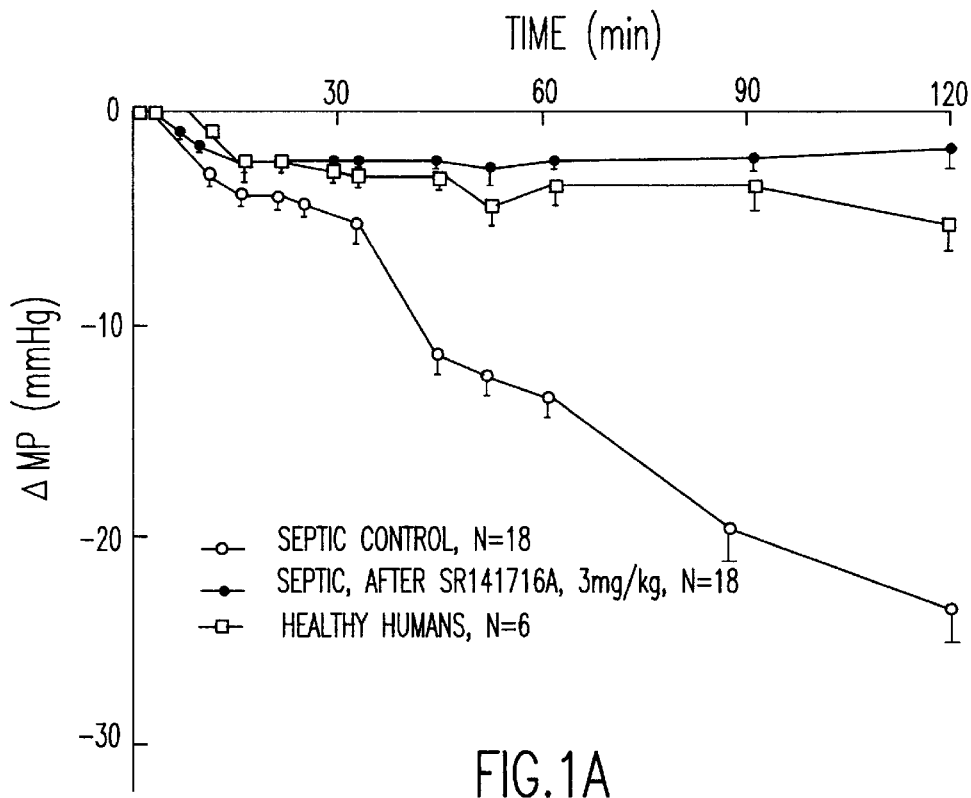
FIGS. 1–11 show several different graphs and the legends of these figures are as follows: Legend for Figures.
Figure 1B:
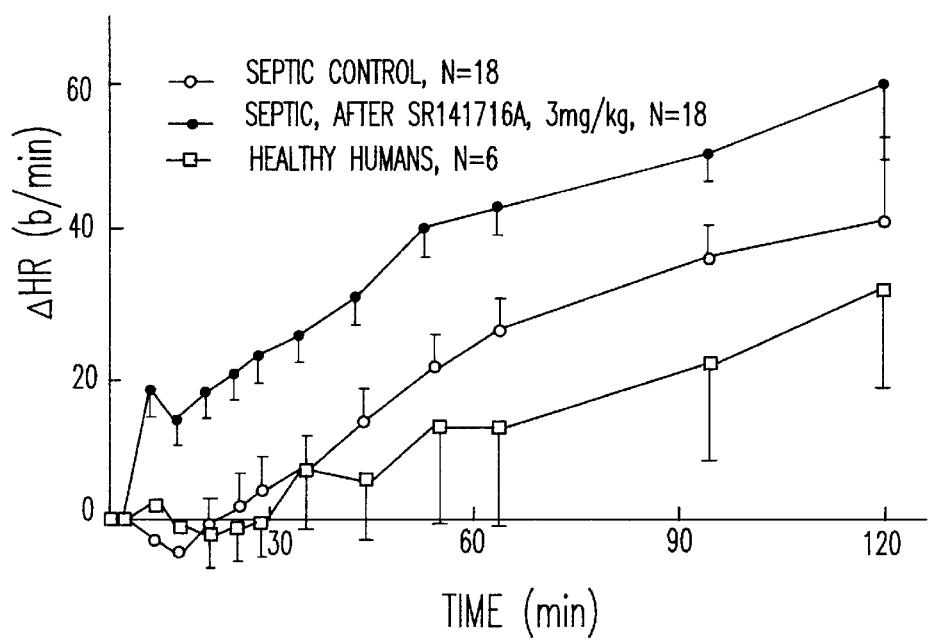

Experiments outlined below show that the use of a drug that selectively blocks CB1 receptors will be of therapeutic value by preventing or attenuating endotoxin-induced hypotension. The related pathological states are septic shock and cirrhosis of the liver. Both of these conditions are known to be associated with elevated blood levels of endotoxin as well as hypotension. In these experiments, monocyte/platelet preparations were obtained from 18 patients with septic shock, and equal aliquots of the isolated cells were infused into a pair of anesthesized Sprague-Dawley rats instrumented to measure blood pressure and heart rate. One rat received 3 mg/kg SR141716A intravenously while the other rat received vehicle pretreatment. Mean arterial pressure (MAP) and heart rate were monitored for 2 hours. Infusion of monocytes/platelets into vehicle-pretreated rats caused a sustained reduction in blood pressure (max: −23±3 mm Hg) and an increase in heart rate, whereas the same infusion into SR141716A-pretreated rats caused only a negligible change in blood pressure (−4±2 mmHg) and an increase in heart rate similar to that in controls (FIG. 1). Monocytes/platelets isolated from healthy humans had no effect on blood pressure or heart rate.

Figure 2A:
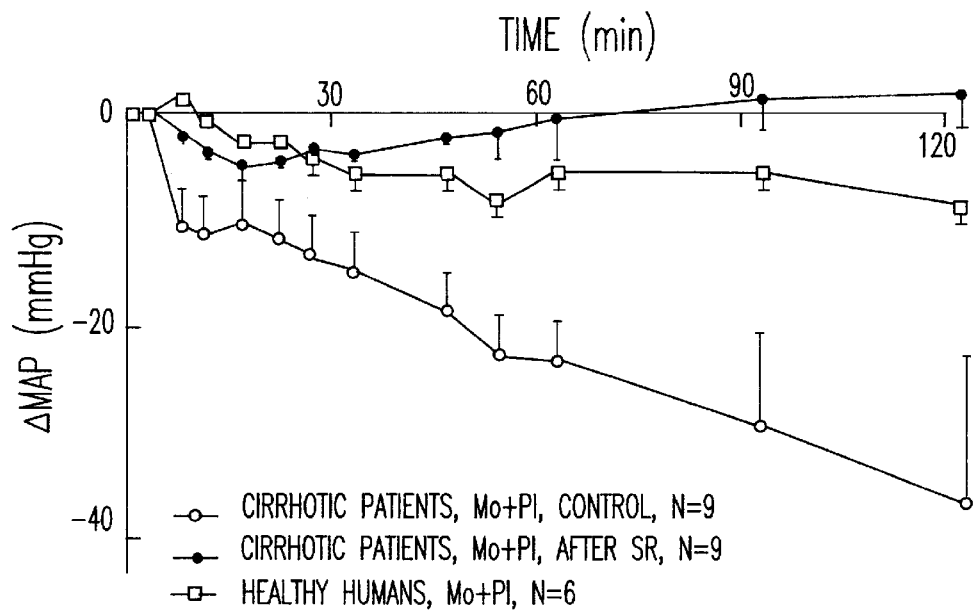
Figure 2B:
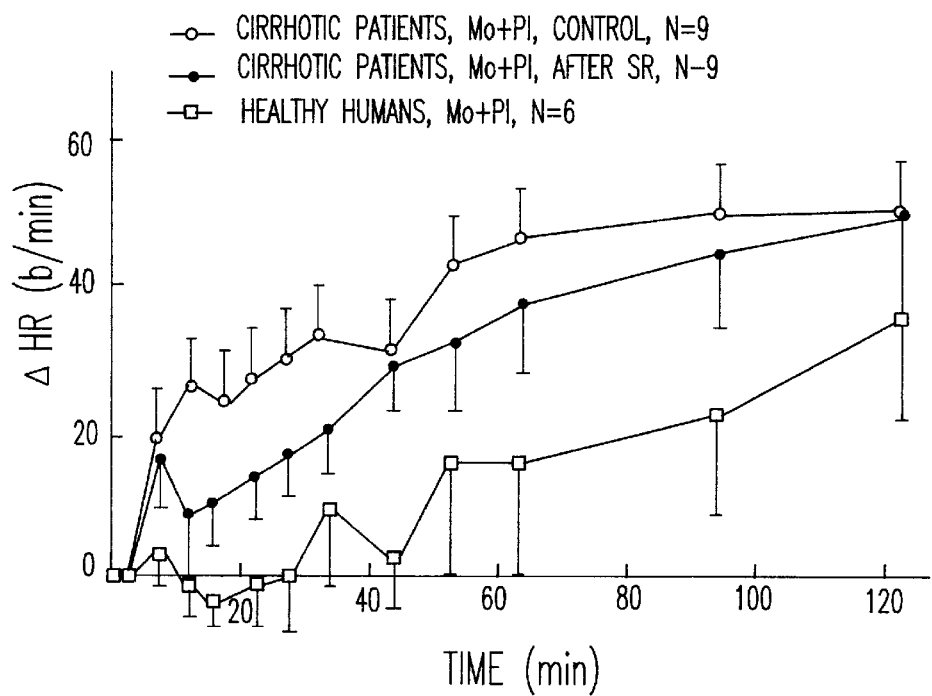

Similar observations were made using monocytes/platelets from 9 patients with chronic liver cirrhosis, a disease associated with elevated plasma levels of endotoxin and severe hypotension. Monocytes/platelets from cirrhotic patients elicited hypotension (max: −38±10 mmHg) and tachycardia in vehicle-pretreated rats, and no significant hypotension but similar tachycardia in SR141716A-pretreated rats (FIG. 2). Again, monocytes and platelets from healthy humans had no effect on blood pressure or heart rate. These observations suggest that monocytes/platelets in patients with septic shock or in those suffering from chronic liver cirrhosis elicit hypotension via the activation of a SR141716A-sensitive receptor (receptor inhibited by SR141716A), whereas the tachycardia effect of these cells does not involve a similar mechanism.

The evidence for a role of CB1 receptors in the above hypotensive conditions is based on the ability of the selective CB1 antagonist, SR141716A, to inhibit or reverse the hypotension. However, additional observations reported herein indicate that SR141716A may also inhibit a unique receptor distinct from the CB1 receptor. Such receptors, rather than the classical CB1 receptors, may mediate endotoxin-induced hypotension and may be targets for the treatment of endotoxin-related hypotension by receptor antagonists.

These results suggest the general applicability of using ligands (i.e., agonists and antagonists) of cannabinoid receptors or cannabinoid-like receptors (i.e., receptors other than CB1) to treat pathological states of hypotension or hypertension in patients, including humans and animals. Sufficient quantities of these ligands should be supplied to the patients by appropriate delivery routes (i.e., i.v., i.p., oral, sublingual, subcutaneous, etc.) to either counteract the hypotension or hypertension pathology.

MATERIALS AND METHODS

Preparation of Rat Isolated, Buffer-Perfused Mesenteric Arterial Bed

Male Sprague-Dawley rats weighing 300–350 g were anesthetized with ether. Following laparotomy, a second order branch of the superior mesenteric artery was cannulated using a PE60 polyethylene cannula. The mesenterium was then isolated following an established procedure, separated from the intestines and placed in a water-jacketed perfusion chamber maintained at 37° C. The preparation was perfused at a rate of 2 mL/min with Krebs-Henseleit solution (composition in mmol/L: NaCl 118, KCl 4.7, $KH_2PO_4$ 1.2, $MgSO_4$ 0.6, $CaCl_2$ 2.5. $NaHCO_3$ 25, glucose 11.7, pH 7.4) pregassed with 95% $O_2$/5% $CO_2$, using a peristaltic pump (Rainin). Perfusion pressure was monitored via a T-tube inserted between the pump and the inflow cannula, and connected to a pressure transducer (Abbott, North Chicago, Ill.) and physiograph (Astromed, Cortland, N.Y.). After an equilibration period of 30 minutes, the perfusion pressure, which was usually 30–40 mmHg at this perfusion rate, was then raised to 80–100 mmHg by the inclusion of phenylephrine (15 µmol/L) in the perfusion medium. Once the perfusion pressure had stabilized, endothelium-dependent and independent vasodilator responses were tested by bolus intra-arterial injections of acetylcholine and sodium nitroprusside, respectively. The magnitude of vasodilation was expressed as percent relaxation, 100% being equal to the phenylephrine-induced contractile response. Unless indicated otherwise, drugs were injected as a bolus close to the artery, in a volume of 100 µL over a period of 5 seconds. In some experiments, rats received an i.p. injection of 15 mg/kg *Escherichia coli* lipopolysaccharide (LPS) two hours prior to removal of the mesenteric bed for the in vitro study.

Endothelial Denudation

To achieve endothelial denudation, the preparation was perfused with distilled water for 3 to 6 minutes or with 0.3% deoxycholate in Krebs-Henseleit buffer for 20–30 seconds. In both cases, phenylephrine was omitted from the medium during these perfusions, and was reintroduced once perfusion pressure became stable. Functional denudation was considered to be achieved when the maximal dilator response to acetylcholine was reduced to <20% of control or converted to a pressor response, while the maximal dilator response to sodium nitroprusside remained unchanged. Only those preparations that met these criteria were used for further testing. Despite carefully controlled experimental conditions, the time of distilled water or detergent perfusion required for denudation remained variable, and the window between incomplete denudation and complete loss of vascular reactivity was found to be narrow. As a result, effective denudation was achieved in less than 20% of the preparations.

Chemicals

SR1 41716A (N-[piperidin-1-yl]-5-[4-chlorophenyl]-1-[1,2-dichlorophenyl]-4-methyl-1Hpyrazole-3-carboxamide HCl) was a gift from Sanofi Co. (Montpellier, France); WIN 55212-2([R]-[+]-[2,3-dihydro-5-methyl-3-{[4-morpholinyl]methyl}pyrrolol[1,2,3-de]1,4-benzoxazin-6-yl]-1 [naphthalenyl)methanone mesylate), R(+)-methanandamide, and $N^G$-Nitro-L-arginine methyl ester hydrochloride (L-NAME) were from RBI (Natick, Mass.); THC ($\Delta^9$-tetrahydrocannabinol) and anandamide (arachidonyl ethanolamide) were kindly provided by Dr. Billy R. Martin, HU-210 ([−]-11-OH-$\Delta^9$-THC) was a gift from Dr. Raphael Mechoulam, 2-arachidonyl glyceride was from Deva Biotech (Hatboro, Pa.). Acetyl-choline, sodium nitroprusside, phenylephrine, arachidonic acid, indomethacin, ionomycin, *E. coli* lipopolysaccharide (0127:B8) and urethane were from Sigma Chemical Co. (St. Louis, Mo.). SR141716A, THC, anandamide and HU-210 were dissolved in 1:1:18 emulphor:ethanol:saline. WIN 55212-2 was dissolved in 1:1:18 emulphor:DMSO:saline. Emulphor is a polyoxyethylated vegetable oil.

Statistical analysis

For comparing agonist effects tested in the same preparations in the absence and in the presence of an antagonist, the paired t test was used. For determining agonist $ED_{50}$ values from graded dose-response curves, the statistical package of Tallarida was used.

Results

Figure 3:
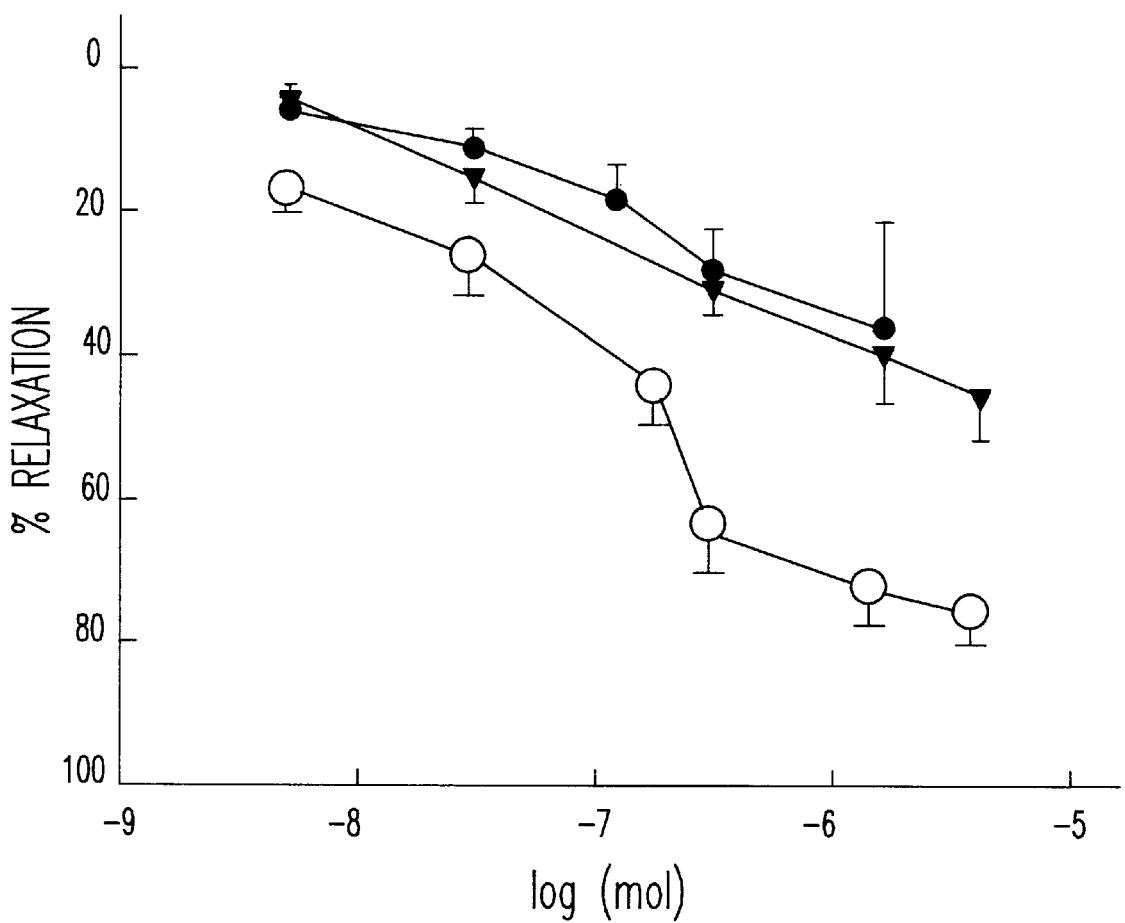
Figure 4A:
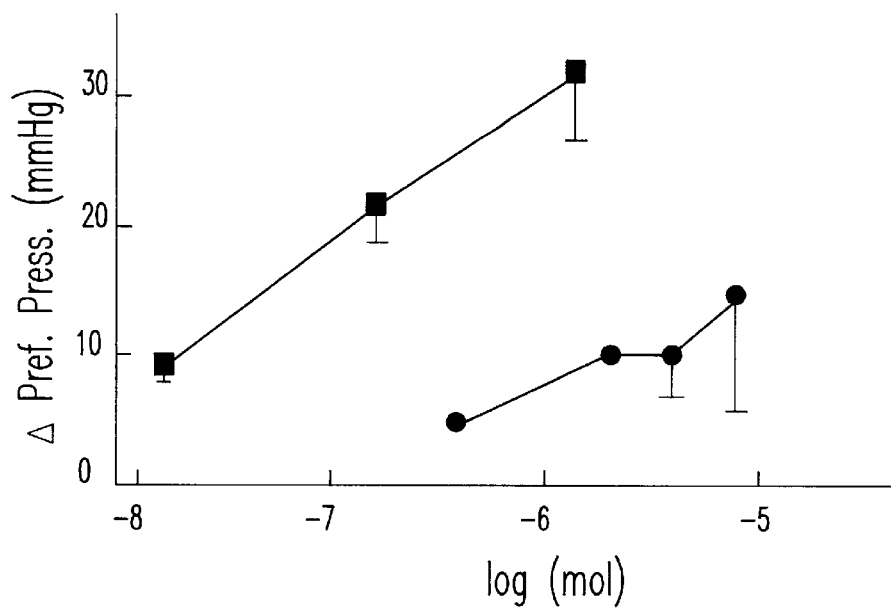
Figure 4B:
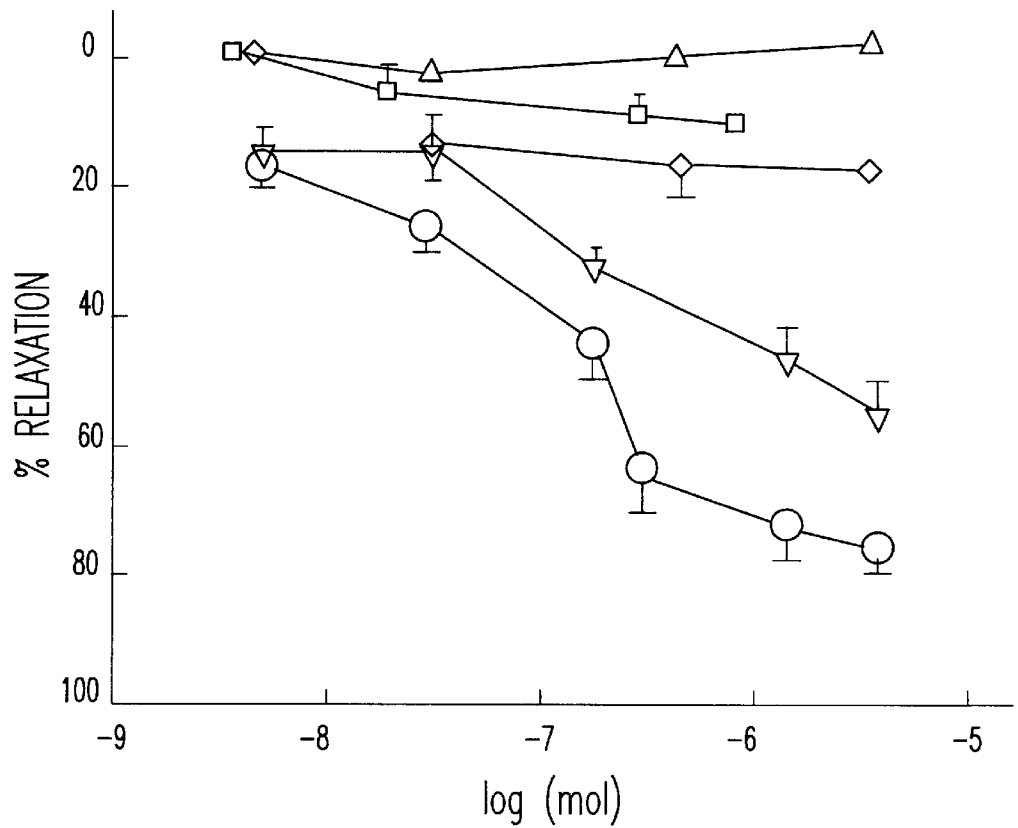

Endotoxin-induced hypotension is due to dilation of the arterioles in various organs, most prominently in the mesenterium that provides the blood supply to the guts. In an isolated, buffer-perfused rat mesenteric vascular bed preparation we found that anandamide elicits pronounced, dose-dependent vasodilation, which is inhibited by low concentrations of SR141716A (FIG. 3). Similar vasodilation was observed with meth-anandamide, a metabolically stable analog of anandamide. However, plant-derived and synthetic cannabinoids, which are known to potently bind to and activate CB1 cannabinoid receptors, had no vasodilator effect in this preparation (FIG. 4). This suggests that, at least in this vascular bed, anandamide causes dilation by a receptor distinct from CB1 receptors, but which is nevertheless sensitive to blockade by SR141716A.

At a concentration of 0.5 $\mu$mol/L, SR141716A significantly inhibited the dilator effect of anandamide to an extent which is comparable to its known antagonism of CB1 receptor-mediated effects (Rinaldi-Carmona et al. 1994, 350:240–244). However, when the concentration of SR141716A was increased 10-fold to 5 $\mu$mol/L, the degree of inhibition increased only twofold, suggesting that additional, SR141716A-insensitive mechanisms also contribute to the vasodilator effect of anandamide (FIG. 3).

Figure 5:
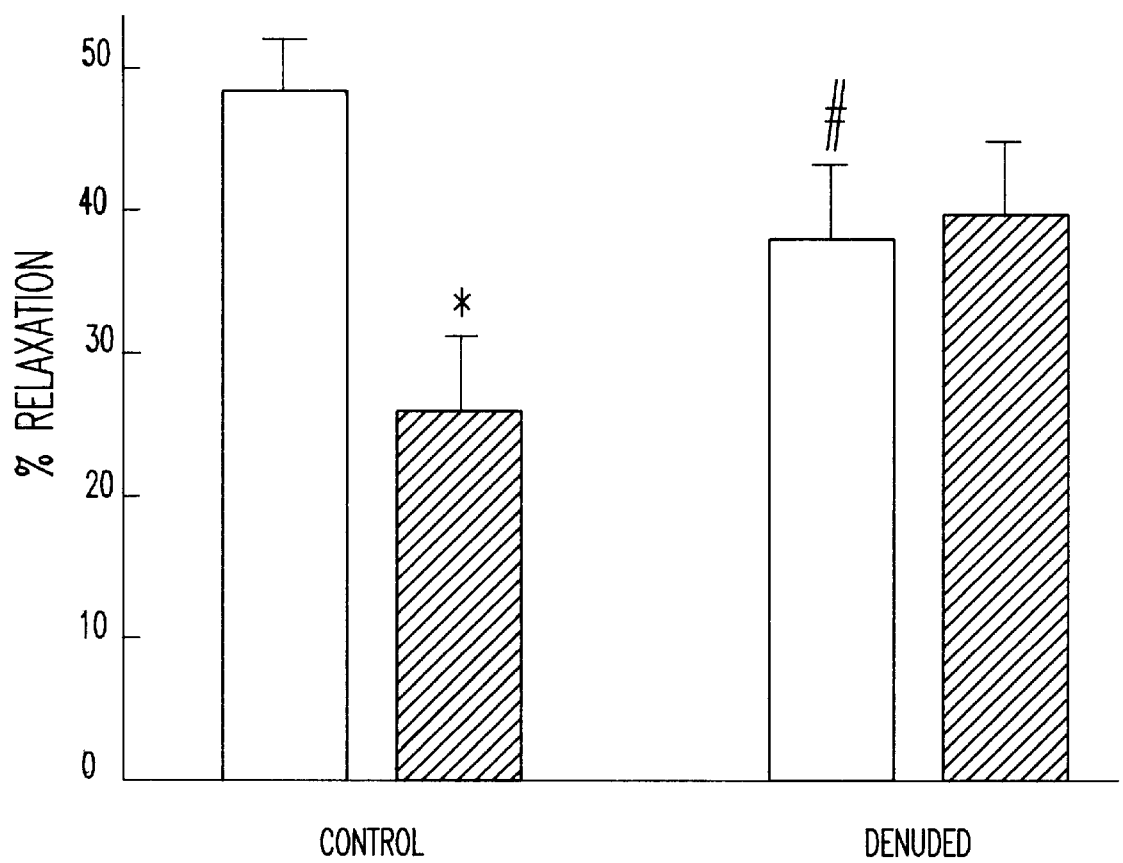
Figure 6A:
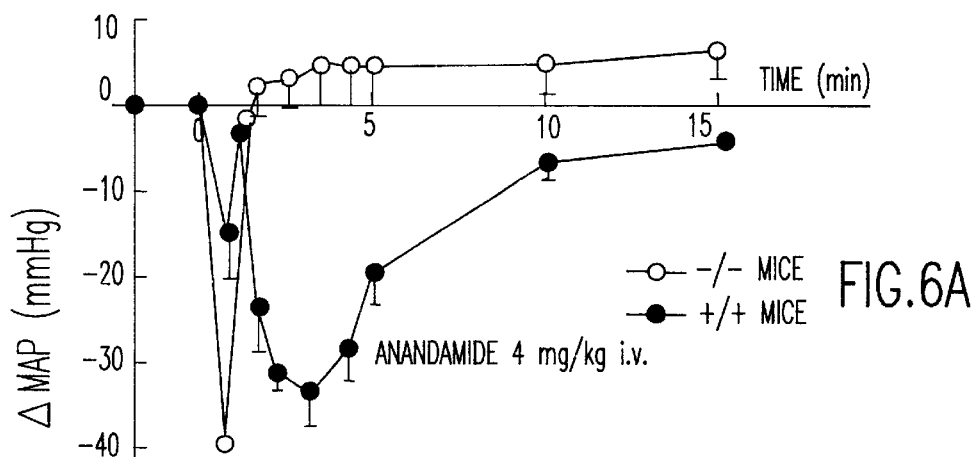
Figure 6B:
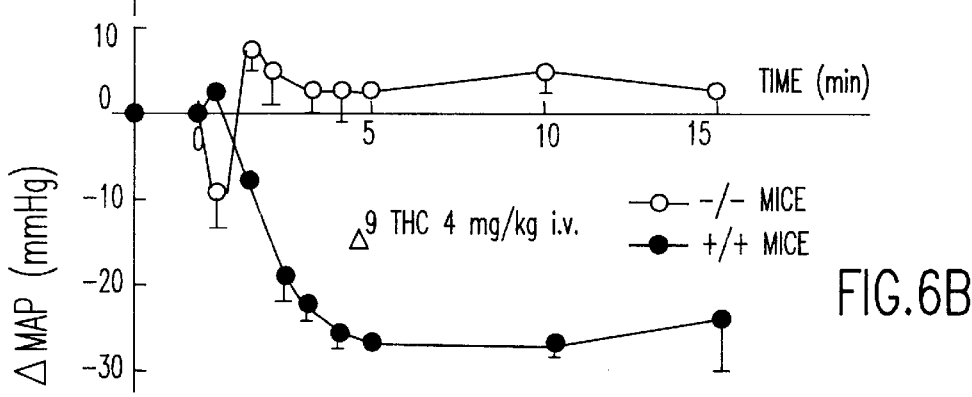
Figure 6C:
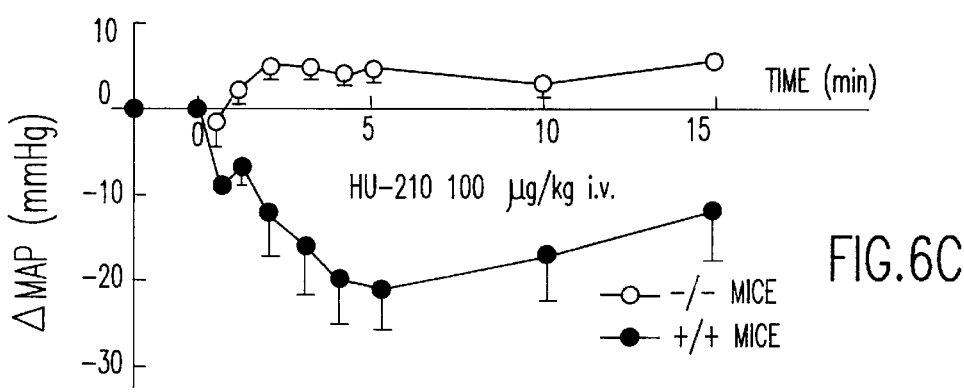
Figure 6D:
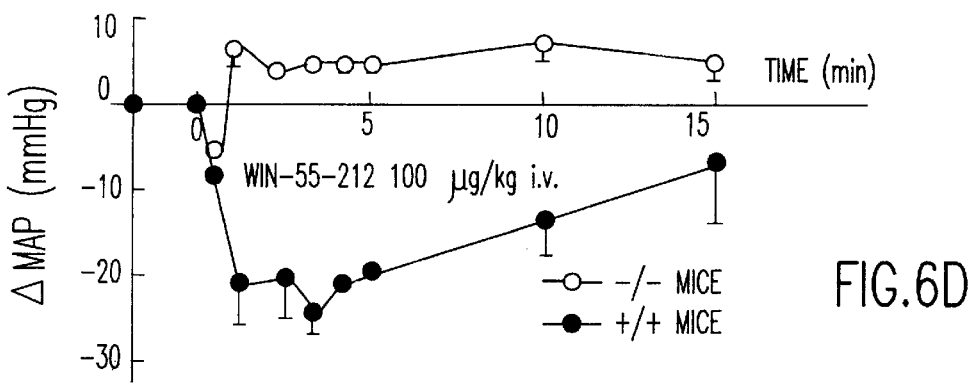

This was supported by results obtained in additional experiments. Since anandamide may act on the endothelium or the vascular smooth muscle, or both, we tested the effects of anandamide in endothelium denuded preparations. In these preparations, anandamide retained its vasodilator action, although the effect was modestly but significantly reduced (FIG. 5). A striking difference between the results obtained with intact versus denuded preparations was, however, that the effect of anandamide after denudation was no longer influenced by SR141716A: the dilator response to 144 nmol of anandamide was 37±5% in the absence and 38±6% in the presence of 5 $\mu$mol/L SR141716A (FIG. 5). These findings suggest that although anandamide is capable of causing vasodilation by a direct effect on smooth muscle, this effect is not mediated by an SR141716A-sensitive receptor.

Figure 7:
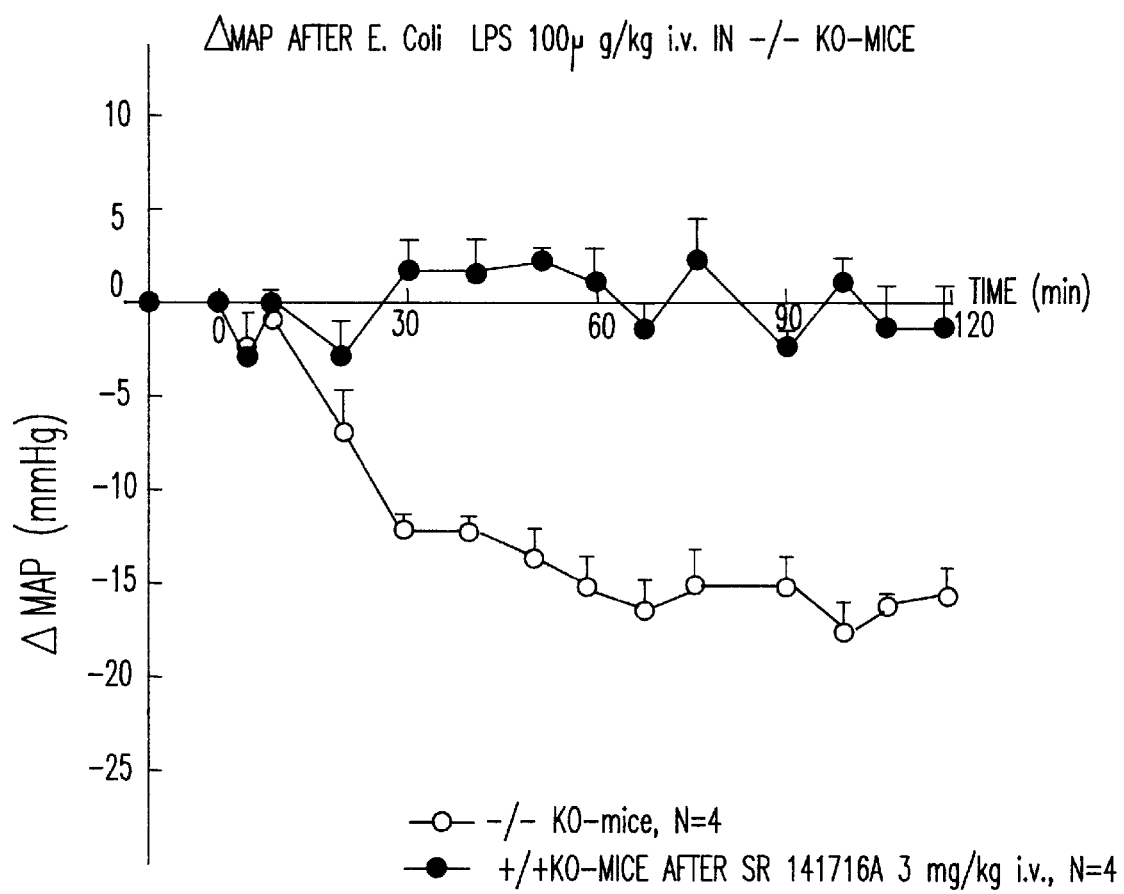

This possibility is further supported by our findings in genetically altered 'knock-out' mice, which are deficient in CB1 receptors due to selective disruption of both alleles of the gene encoding this receptor (−/− mice). In the genetically matched controls homozygous for normal CB1 receptors (+/+ mice), anandamide as well as plant-derived ($\Delta^9$-THC) and synthetic cannabinoids (HU-210, WIN 55212-2) cause pronounced hypotension (FIG. 6, filled circles), whereas in the −/− knockout mice none of the 4 agonists causes any hypotension (FIG. 6, open circles), which confirms the role of CB1 receptors in these effects. However, low doses of LPS (0.1–1 mg/kg i.p.) still cause prolonged hypotension in the −/− mice, and this effect can be prevented by pretreatment of the animals with 3 mg/kg SR141716A (FIG. 7). These observations suggest that the LPS-induced hypotension is mediated by an SR141716A-sensitive receptor distinct from the CB1 receptor, and possibly similar to the receptor mediating the mesenteric vasodilator effect of anandamide. Based on these findings, we propose that in septic shock, the use of a drug that selectively blocks CB1-like receptors (e.g., an anandamide receptor) will be effective in preventing or attenuating endoxotin-induced hypotension.

In a preferred embodiment of this invention, the CB1 receptor antagonist SR141716A will be administered to patients suffering from severe cirrhosis for reversing the associated hemodynamic abnormality of hypotension. Cirrhosis affects 3.6 per 1000 adults in North America and causes over 32,000 deaths and 20 million days of work loss annually. Much of this morbidity and mortality is due to the hemodynamic consequences of cirrhosis on portal and systemic circulation. The principal effect of cirrhosis on portal circulation is the development of portal hypertension. Portal hypertension has two components. First, it is initiated by an increase in outflow resistance through the portal system by distortion of the sinusoidal circulatory bed by scar tissue in cirrhosis. Second, and even more importantly, cirrhosis is associated with mesenteric ateriolar vasodilation which increases portal inflow. Portal pressure, the product of portal flow and outflow resistance, thus rises dramatically in patients with cirrhosis. The primary consequence of portal hypertension is the development of varices which can bleed; this causes a third of all deaths related to cirrhosis. While several pharmacological agents have been used to increase mesenteric arterial resistance in order to decrease portal flow and thus treat portal hypertension, they have met with only mixed success. In systemic circulation, the principal effect of cirrhosis is one of progressive vasodilation. This decreases the effective circulating volume of blood and activates Na-retentive mechanisms which lead to Na (sodium) and water retention and ascites, the most common complication of cirrhosis. As cirrhosis progresses, the vasodilated state worsens with decreasing mean artierial pressure, increased cardiac output and marked Na retention and eventually renal failure and death.

It is therefore apparent that a vasodilatory state plays a key role in the pathogenesis of the two principal causes of morbidity and mortality in cirrhosis. Although a number of mediators have been implicated, no single agent has been clearly shown to be primarily responsible for the vasodilatory state. Moreover, antagonists to these agents have not successfully reversed the hemodynamic abnormalities in cirrhotic individuals. In addition, numerous studies have documented that endotoxin levels in the systemic as well as the portal circulation are increased in patients with cirrhosis compared to those with milder degrees of other liver diseases or healthy individuals (Lin et al. *J. Hepatol.* 1995, 22:165–172). It is also well-established that the endotoxin levels are higher in those with more advanced cirrhosis who also have greater degrees of systemic and splanchic vasodilation, larger varices, greater ascites and poorer liver function (Chan et al. *Scand. J. Gas.* 1997, 32:942–946). It has been proposed that increased endotoxin levels increase nitric oxide (NO) production by increasing NO synthase (NOS) activity. However, experimental studies in animal models indicate that NOS activity is not increased in those with cirrhosis. It is therefore apparent that if elevated endotoxin levels and hemodynamic changes in patients with advanced cirrhosis are causally related, this in not via NO related hypotension.

Based on our investigations, we conclude that the vasodilation in patients with cirrhosis is due in large measure to the production of cannabanoids by platelets/macrophages and that the vasodilated state can be reversed by an antagonist for a cannabinoid receptor (CB1 and CB1-like receptors being collectively referred to herein as canabinoid receptors). In particular, good results can be obtained with the CB1 receptor antagonist, SR141716A, which is available from Sanofi, Inc. The antagonist can be administered by a variety of different routes. The preferred delivery route is oral. The dose will depend on a number of factors including the age, gender, and previous medical history of the patient. It is expected that doses of 0.5–2 mg/kg will have beneficial effects; however, selection of the dose can vary widely. In the clinical setting with human subjects, we suggest measuring the effects of SR141716A on pulse rate, blood pressure, portal venous flow, mesenteric arteriolar resistance, hepatic arterial flow, hepatic blood flow, and portal venous pressure. For example, patient response to the drug could be monitored by measurement of blood pressure at regular (eg. 10 minute) intervals.

While the experiments above show the effects of the CB1 receptor antagonist SR141716A, it will be clear to one of skill in the art that a wide variety of other CB1 receptor antagonists (or antagonists of CB1-like receptors) could be used in the practice of this invention because the evidence presented indicates that the activation of CB1-like receptors mediates the hypotension of septic shock, and reversing hypotension is a primary goal of treatment. There are a number of well known antagonists for use in the practice of this invention (e.g. LY320135). Other examples of CB1 receptor antagonists can be found in U.S. Pat. No. 5,596,106 and U.S. Pat. No. 5,747,524, both of which are herein incorporated by reference.

In similar fashion, the agonists of CB1 receptors or CB1-like receptors could be used to treat conditions associated with excessive vasoconstriction, such as hypertension, peripheral vascular disease or angina pectoris. As cited previously (Lake et al.), CB1 agonists are known to lower blood pressure. However, CB1 agonists also elicit potent neurobehavioral ('marijuana-like') effects by activating CB1 receptors in the brain (Compton et al., *J. Pharmacol. Exp. Ther.* 1996, 277:586–594), which limits their clinical usefulness. This problem could be circumvented by using agonists that activate vascular CB1-like receptors without activating CB1 receptors in the brain. There is evidence that activation of CB1-like receptors in hemorrhagic shock is not associated with marijuana-like effects, such as hypothermia and analgesia (Wagner et al.).

Figure 8:
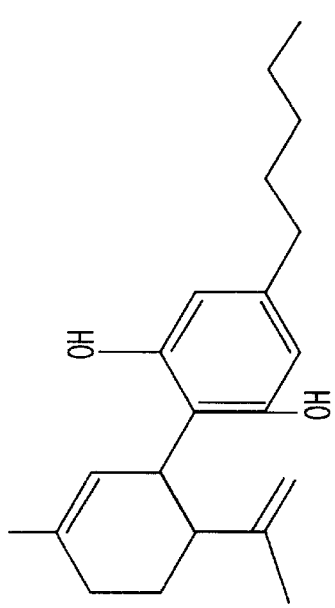
Figure 8:
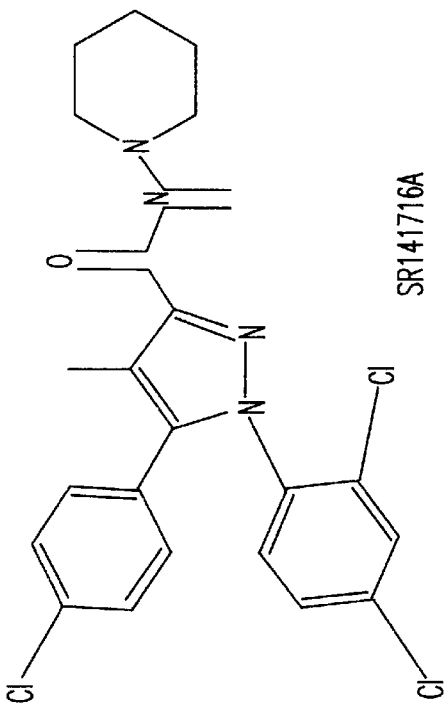
Figure 8:
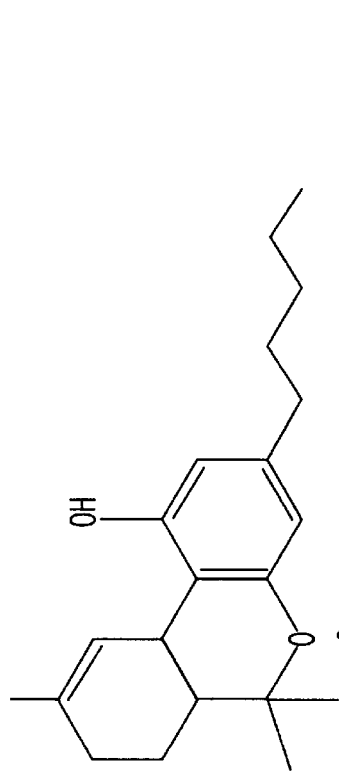
Figure 8:
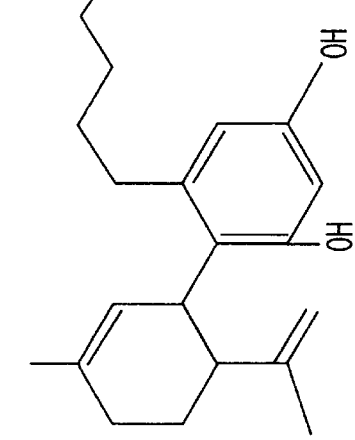
Figure 8:
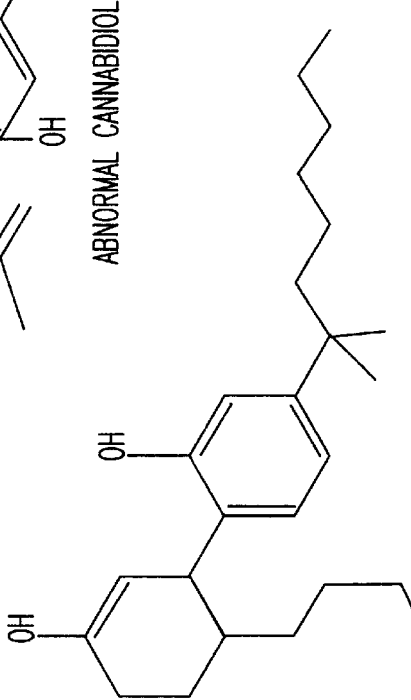
Figure 9A:
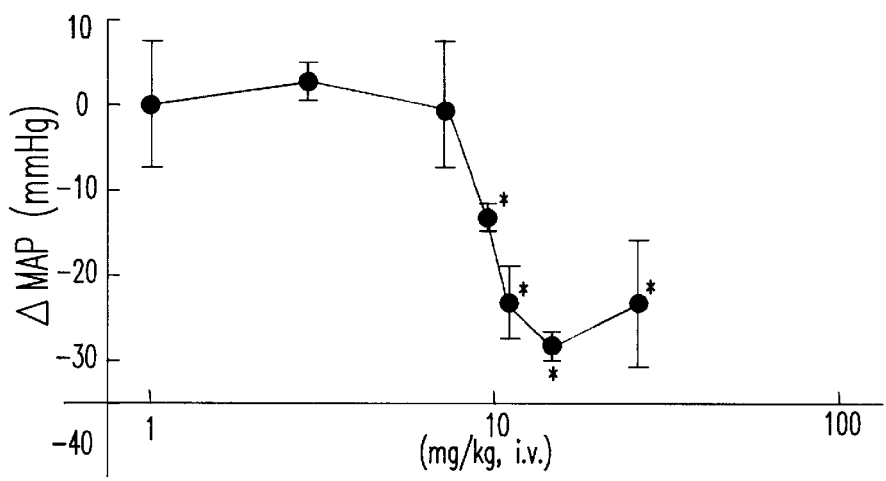
Figure 9B:
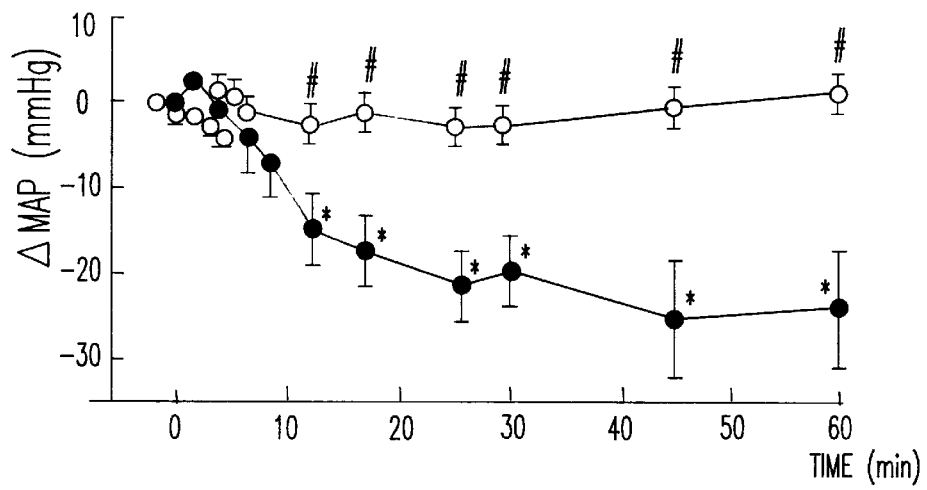
Figure 9C:
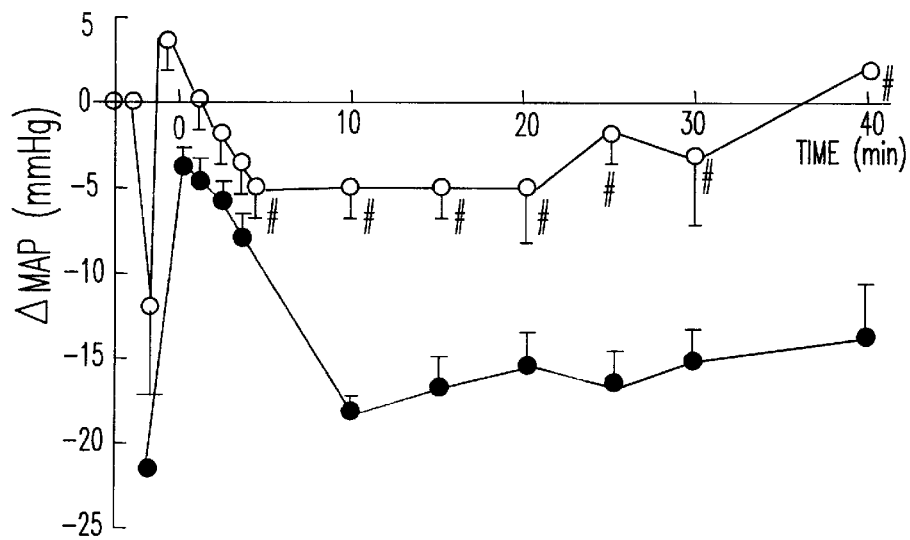
Figure 10:
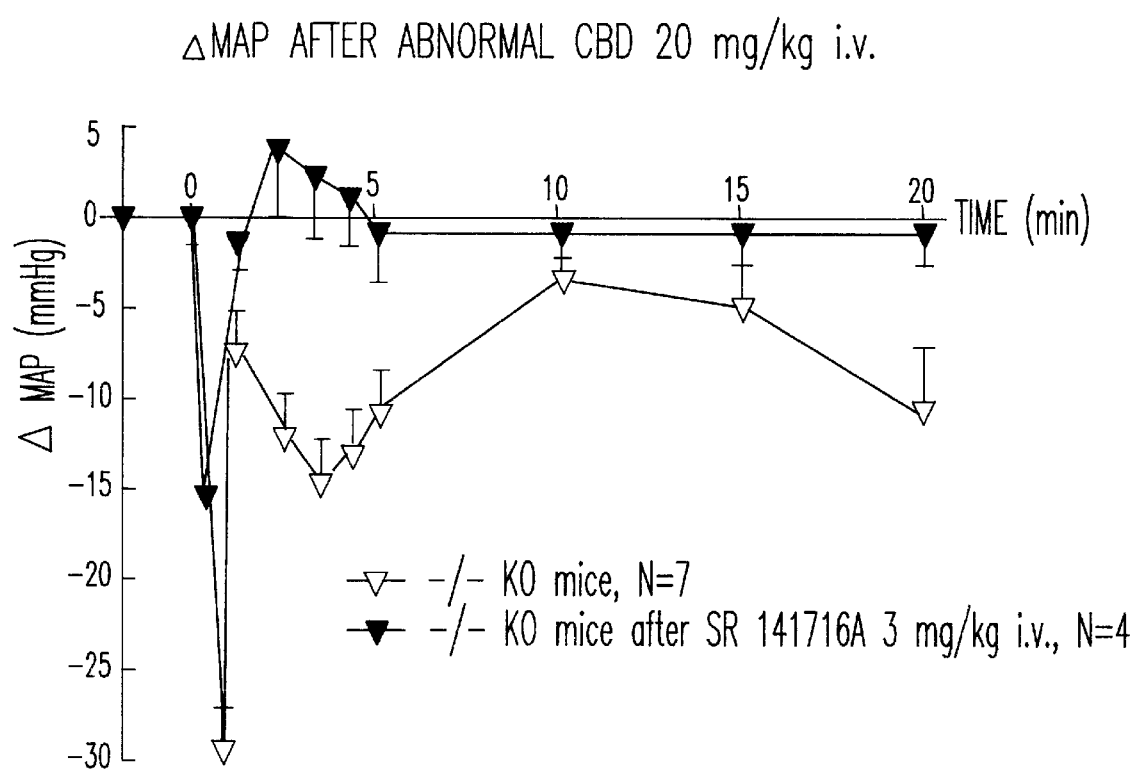
Figure 11:
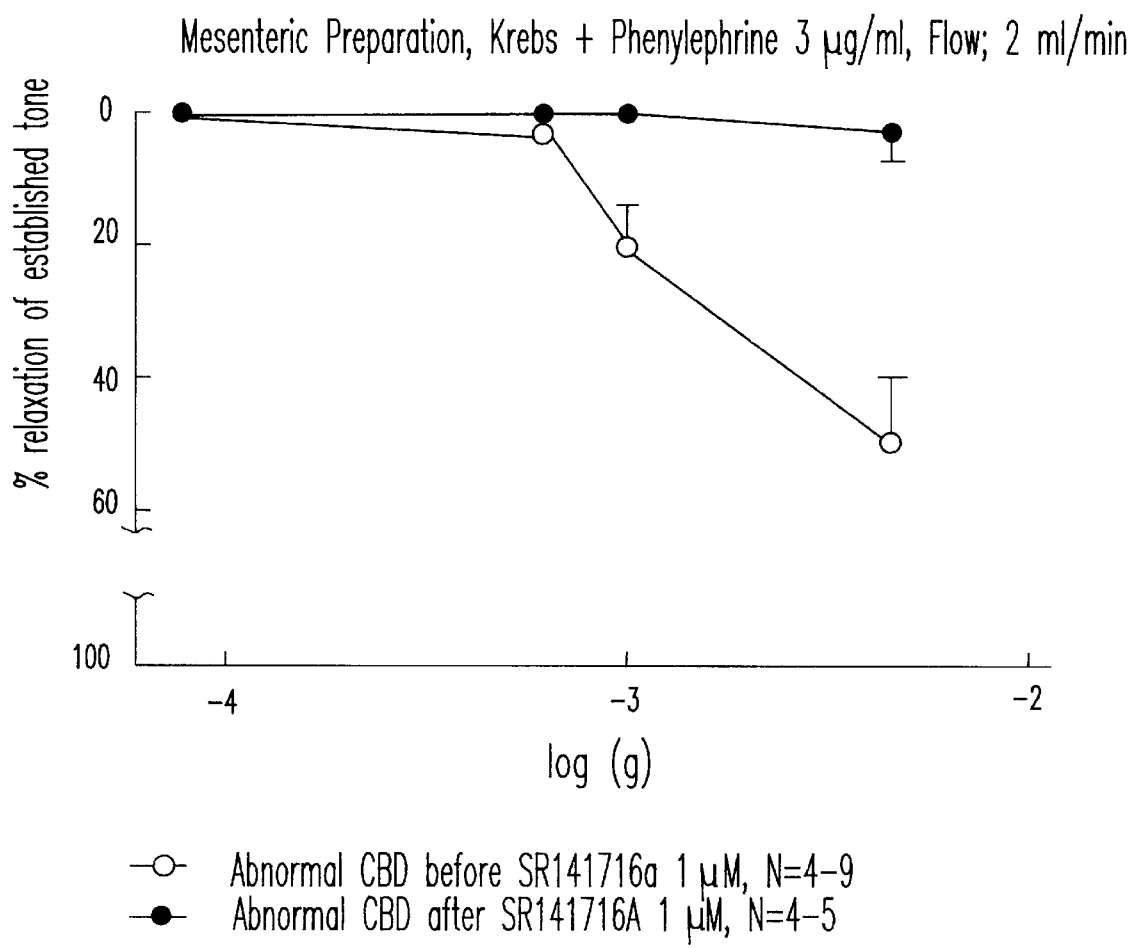

Our recent findings indicate that the compound 'abnormal cannabidiol' (Adams et al., *Experientia* 1977, 33:1204–1205, see also structure in FIG. 8) may be a selective agonist of CB1-like receptors, and does not interact with CB1 receptors. In both anesthetized rats and mice, 10 mg/kg (i.v.) of abnormal cannabidiol (abnCBD) was found to cause hypotension that could be prevented by pretreatment of the animals with 3 mg/kg SR141716A (FIG. 9). AbnCBD elicited similar although shorter lasting hypotension, inhibited by SR141716A, in CB1 receptor knockout –/– mice (FIG. 10). Furthermore, in the perfused rat mesenteric vascular bed preparation (in which potent CB1 agonists were found to be inactive), abnCBD caused vasodilation which could be inhibited by SR141716A (FIG. 11). These last two findings indicate that abnCBD induces hypotension via CB1-like (non-CB1) receptors. In other experiments it was found that abnCBD in doses up to 60 mg/kg does not cause marijuana-like neurobehavioral effects in mice (Table 1). Furthermore, using an in vitro ligand binding assay (Compton et al., *J. Pharmacol. Exp. Ther.* 1993, 265:218–226), abnCBD at concentrations up to 100 uM failed to displace [$^3$H]CP-55,940 (a potent known ligand of CB1 receptors) from CB1 cannabinoid receptors in a rat brain plasma membrane preparation, a finding replicated 3 times. Saturation experiments of [$^3$H]CP-55,940 binding (n=6) revealed a $K_d$ of 809±21 pM, a $B_{max}$ (total number of ligand binding sites) of 1.2 pmol/mg protein, and a Hill coefficient of 0.94±0.05, values similar to those obtained previously by Compton (et al., 1993). These latter findings indicate that abnCBD is not an agonist of CB1 receptors.

TABLE 1

In vivo effects of abn-CBD in the mouse model of cannabinoid activity

| Dose (mg/kg) | locomotor activity (% inhibition) | antinocieption (% MPE) | core temperature (Δ ° C.) | immobility (%) |
|---|---|---|---|---|
| 0 | 0 ± 0 | 6 ± 3 | 0.5 ± 0.1 | 0 ± 0 |
| 10 | 0 ± 5 | 4 ± 2 | 0.3 ± 0.3 | 0 ± 0 |
| 30 | 0 ± 10 | 6 ± 6 | 0.4 ± 0.1 | 0 ± 0 |
| 60 | 6 ± 16 | 13 ± 3 | -0.5 ± 0.9 | 0 ± 0 |

The above four parameters were measured as described in detail by Compton et al. (1996). Briefly, spontaneous locomotor activity is expressed as % inhibition vs. control. Mice were placed in individual activity cages 5 minutes post treatment, and interruption of the photocell beams (16 beams/chamber) were recorded for a 10 minute period usng a Digiscan Animal Activity Monitor (Omnitech). The degree of antinocieption (tail flick latency) is expressed as % of maximal possible effect (MPE). The heat lamp was maintained at an intensity sufficient to produce control latencies of 2–3 seconds. Latency values for each animal were determined before treatment and 20 minutes following treatment with abnCBD. A 10-second maximum latency was imposed to prevent tissue damage. % MPE was calculated as:

$$\frac{(\text{test latency}) - (\text{control latency})}{(10 \text{ sec.} - \text{test latency})} \times 100$$

Core temperature was measured by a rectal thermistor inserted to 25 mm, before and 30 minutes after administration of abnCBD. Catalepsy (ring immobility procedure) was expressed as % of total time spent motionless. Mean values and their standard errors are shown. The number of animlas tested in each of the 4 paradigms was 6–12. None of the values is significantly different from the corresponding drug-free control value.

Therefore, in a second preferred embodiment of this invention, the non-CB1 receptor (cannabinoid receptor other than CB1) agonist abnCBD could be administered to patients suffering from diseases related to excessive vasocontriction. Administration could be by a variety of routes and the dose would depend on a number of factors, including the age, gender and previous medical history of the patient. In the clinical setting with human subjects, we suggest measuring the effects of SR141716A on pulse rate, blood pressure, portal venous flow, mesenteric arteriolar resistance, hepatic arterial flow, hepatic blood flow, and portal venous pressure. For example, patient response to the drug couldl be monitored by measurement of blood pressure at regular (eg. 10 minute) intervals.

While the experiments above suggest the effects of the non-CB1 receptor agonist abnCBD, it will be clear to one of skill in the art that a wide variety of related compounds are available for testing or to serve as prototypes for derivatization in order to convert them to pharmaceutically useful non-CB1 cannabinoid receptor agonists. Examples of CB1 receptor agonists which can be used in the practice of this invention can be found in U.S. Pat. No. 5,532,237, U.S. Pat. No. 5,605,906, and U.S. Pat. No. 5,631,297, all of which are herein incorporated by reference.

While the invention has been described in terms of its preferred embodiments, those skilled in the art will recognize that the invention can be practiced with modification within the spirit and scope of the appended claims.

We claim:

1. A method for the treatment of pathological states in patients associated with hypotension or hypertension, comprising the step of administering to a patient in need thereof a sufficient amount of a ligand of a cannabinoid receptor, wherein said cannabinoid receptor is selected from the group consisting of CB1 receptors, CB1-like receptors and anandamine receptors, and, wherein said ligand is selected from the group consisting of agonists and antagonists.

2. The method of claim 1 wherein said cannabinoid receptor is CB1.

3. The method of claim 1 wherein said cannabinoid receptor is a receptor other than CB1.

4. The method of claim 1 wherein said ligand is an antagonist of CB1.

5. The method of claim 1 wherein said ligand is an agonist of CB1.

6. The method of claim 1 wherein said ligand is an antagonist of a cannabinoid receptor other than CB1.

7. The method of claim 1 wherein said ligand is an agonist of a cannabinoid receptor other than CB1.

* * * * *

UNITED STATES PATENT AND TRADEMARK OFFICE
CERTIFICATE OF CORRECTION

PATENT NO. : 5,939,429
DATED : August 17, 1999
INVENTOR(S) : Kunos et al.

It is certified that error appears in the above-identified patent and that said Letters Patent is hereby corrected as shown below:

Column 1, line 3, below the title, please add --This work was partially funded by NIH grant no. HL59257, the government may have certain rights in this invention--.

Signed and Sealed this

Twenty-eighth Day of November, 2000

Attest:

Q. TODD DICKINSON

Attesting Officer

Director of Patents and Trademarks